US009060741B2

(12) United States Patent
Fuse et al.

(10) Patent No.: US 9,060,741 B2
(45) Date of Patent: Jun. 23, 2015

(54) MOBILE X-RAY DEVICE, CONTROL METHOD FOR X-RAY IRRADIATION, AND CONTROL PROGRAM FOR MOBILE X-RAY DEVICE

(75) Inventors: Miyuki Fuse, Tokyo (JP); Tomokazu Takae, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 618 days.

(21) Appl. No.: 13/392,585

(22) PCT Filed: Aug. 2, 2010

(86) PCT No.: PCT/JP2010/063002
§ 371 (c)(1),
(2), (4) Date: Feb. 27, 2012

(87) PCT Pub. No.: WO2011/024608
PCT Pub. Date: Mar. 3, 2011

(65) Prior Publication Data
US 2012/0163543 A1    Jun. 28, 2012

(30) Foreign Application Priority Data
Aug. 28, 2009 (JP) ................................ 2009-197995

(51) Int. Cl.
*H05G 1/10* (2006.01)
*A61B 6/00* (2006.01)

(52) U.S. Cl.
CPC ............ *A61B 6/586* (2013.01); *A61B 6/4405* (2013.01); *A61B 6/461* (2013.01); *A61B 6/467* (2013.01); *A61B 6/542* (2013.01); *H05G 1/10* (2013.01)

(58) Field of Classification Search
CPC ...... A61B 6/4405; A61B 6/461; A61B 6/467; A61B 6/542; A61B 6/586; H05G 1/10; H05G 1/54; H05G 1/265; H05G 1/34

USPC .............................. 378/118, 96, 98, 102, 114
See application file for complete search history.

(56) References Cited

U.S. PATENT DOCUMENTS 5,612,985 A * 3/1997 Toki et al. .................... 378/4
(Continued)

FOREIGN PATENT DOCUMENTS

| JP | 07-299054   | 11/1995 |
| JP | 10-043170   | 2/1998  |
| JP | 2001-145625 | 5/2001  |
| JP | 2003-310595 | 11/2003 |

(Continued)

OTHER PUBLICATIONS

International Search Report for PCT International Application No. PCT/JP2010/063002, mailed on Sep. 14, 2010.

*Primary Examiner* — David J Makiya
*Assistant Examiner* — John Corbett
(74) *Attorney, Agent, or Firm* — Brundidge & Stanger, P.C.

(57) ABSTRACT

Provided is an X-ray device which can perform X-ray imaging without an object being subjected to ineffective exposure even when the X-ray imaging is interrupted by the occurrence of an error. The X-ray device is provided with an X-ray generator, an operation panel configured to set an imaging condition, an X-ray irradiation control unit configured to control X-ray irradiation in accordance with the imaging condition, an error detecting unit, configured to, during the X-ray irradiation, detect the occurrence of an error by which the X-ray irradiation should be interrupted, an irradiation interrupting unit configured to interrupt the X-ray irradiation when the occurrence of the error is detected, and a recovery unit configured to resume the X-ray irradiation for ensuring the X-ray amount defined by the imaging condition.

7 Claims, 7 Drawing Sheets

(56) References Cited

U.S. PATENT DOCUMENTS

| | | | |
|---|---|---|---|
| 6,449,337 B1 * | 9/2002 | Honda et al. | 378/117 |
| 2003/0076920 A1 | 4/2003 | Shinno et al. | |
| 2003/0198317 A1 | 10/2003 | Nakagawa et al. | |
| 2010/0172468 A1 * | 7/2010 | Gregerson | 378/20 |

FOREIGN PATENT DOCUMENTS

| | | | |
|---|---|---|---|
| JP | 2004-055314 | | 2/2004 |
| JP | 2004-259504 | | 9/2004 |
| JP | 2005270224 A | * | 10/2005 |
| JP | 2008-183222 | | 8/2008 |

* cited by examiner

MOBILE X-RAY DEVICE, CONTROL METHOD FOR X-RAY IRRADIATION, AND CONTROL PROGRAM FOR MOBILE X-RAY DEVICE

FIELD OF THE INVENTION

The present invention relates to a mobile X-ray device, a control method for X-ray irradiation, and a control program for a mobile X-ray device, in particular to the technique for suppressing ineffective radiation exposure subjected to an object to be examined.

DESCRIPTION OF RELATED ART

Patent Document 1 discloses the mobile X-ray device equipped with an X-ray tube and an image processing device on a mobile carriage comprising wheels for driving.

PRIOR ART DOCUMENTS

Patent Document 1: JP-A-1995-299054

Generally, X-ray imaging tends to be often interrupted due to various errors which occur during imaging. For example, there is a type of mobile X-ray device configured to be driven by batteries so that X-ray imaging can be performed even in places where an electric power supply cannot be provided. However, X-ray imaging by this type of the mobile X-ray device tends to be interrupted which can be attributed to a shortage of tube voltage, due to fluctuation of discharge output from the batteries caused by ambient temperature (room temperature) or lowering of stored battery energy caused by battery's deterioration due to age. Also, X-ray imaging is interrupted due to occurrence of arcing which is not enough to cause breakage of an X-ray tube. When X-ray imaging is resumed after these interruptions, generation of ineffective exposure from the start of X-ray imaging to the interruption has been a problem.

Considering the above-described problem, the objective of the present invention is to provide a mobile X-ray device, the control method for X-ray irradiation and the control program for a mobile X-ray device capable of performing X-ray imaging without generating ineffective exposure subjected to an object even in the case that the X-ray imaging is interrupted due to occurrence of an error.

BRIEF SUMMARY OF THE INVENTION

In order to achieve the above-described objective, the mobile X-ray device related to the present invention comprises:
a main unit; and
a traveling unit configured to make the main unit run,
wherein the main unit comprises:
an imaging condition setting unit configured to set the imaging condition to be applied to X-ray imaging;
an X-ray generator configured to irradiate an X-ray according to the set imaging condition;
an error detection unit configured to detect the occurrence of an error by which the X-ray irradiation should be interrupted;
an irradiation interrupting unit configured to interrupt the X-ray irradiation when the occurrence of the error is detected; and
a recovery unit configured to resume the X-ray irradiation for ensuring the X-ray amount defined by the imaging condition. The recovery unit, for example irradiates an X-ray by setting the irradiation time of the X-ray to be resumed based on the X-ray amount defined by the imaging condition, or irradiates an X-ray by correcting the set imaging condition.

Also, the control method for X-ray irradiation includes:
a step of receiving the input of an imaging condition;
a step of detecting occurrence of an error by which the X-ray irradiation should be interrupted;
a step of interrupting the X-ray irradiation when the occurrence of an error is detected; and
a step of ensuring the X-ray amount defined by the imaging condition and resuming the X-ray irradiation.

Also, the control program for the mobile X-ray device related to the present invention causes a computer to execute:
a step of receiving the input of the imaging condition to be used for X-ray imaging;
a step of detecting occurrence of an error by which the X-ray irradiation should be interrupted;
a step of interrupting the X-ray irradiation when the occurrence of an error is detected; and
a step of ensuring the X-ray amount defined by the imaging condition and resuming the X-ray irradiation.

In accordance with the present invention, even when X-ray imaging is interrupted, since the recovery process is executed for resuming the X-ray imaging which saves the re-imaging from the start, it is possible to reduce ineffective irradiation subjected to an object and save an operator the effort of restarting X-ray imaging.

BRIEF DESCRIPTION OF THE DIAGRAMS

DETAILED DESCRIPTION OF THE INVENTION

Figure 1:
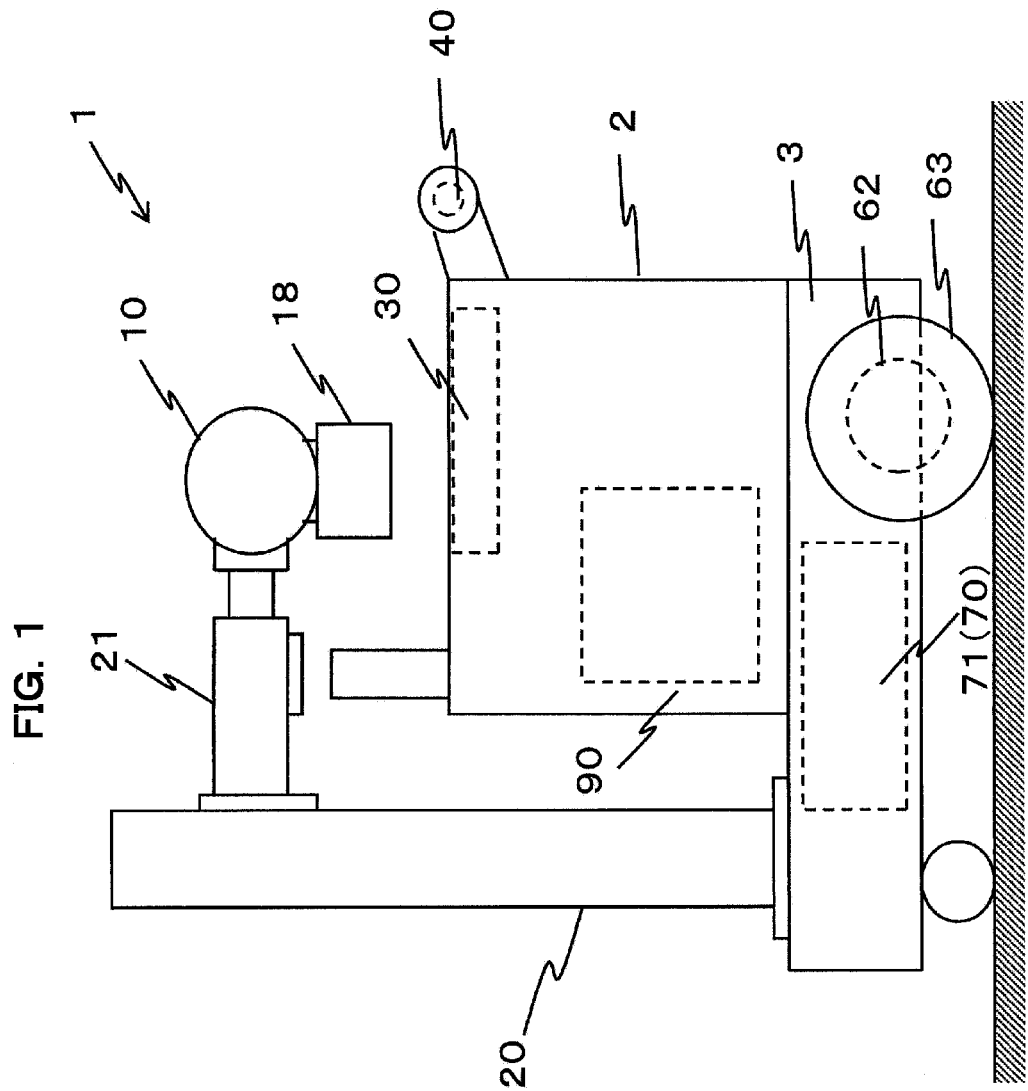
FIG. 1 is an external view of the mobile X-ray device related to the present embodiment.

The embodiment to which the present invention is applied will be described below. In the following diagrams for explaining the embodiment of the present invention, the same function parts are represented by the same reference numerals, and the duplicative description thereof is omitted.

Figure 2:
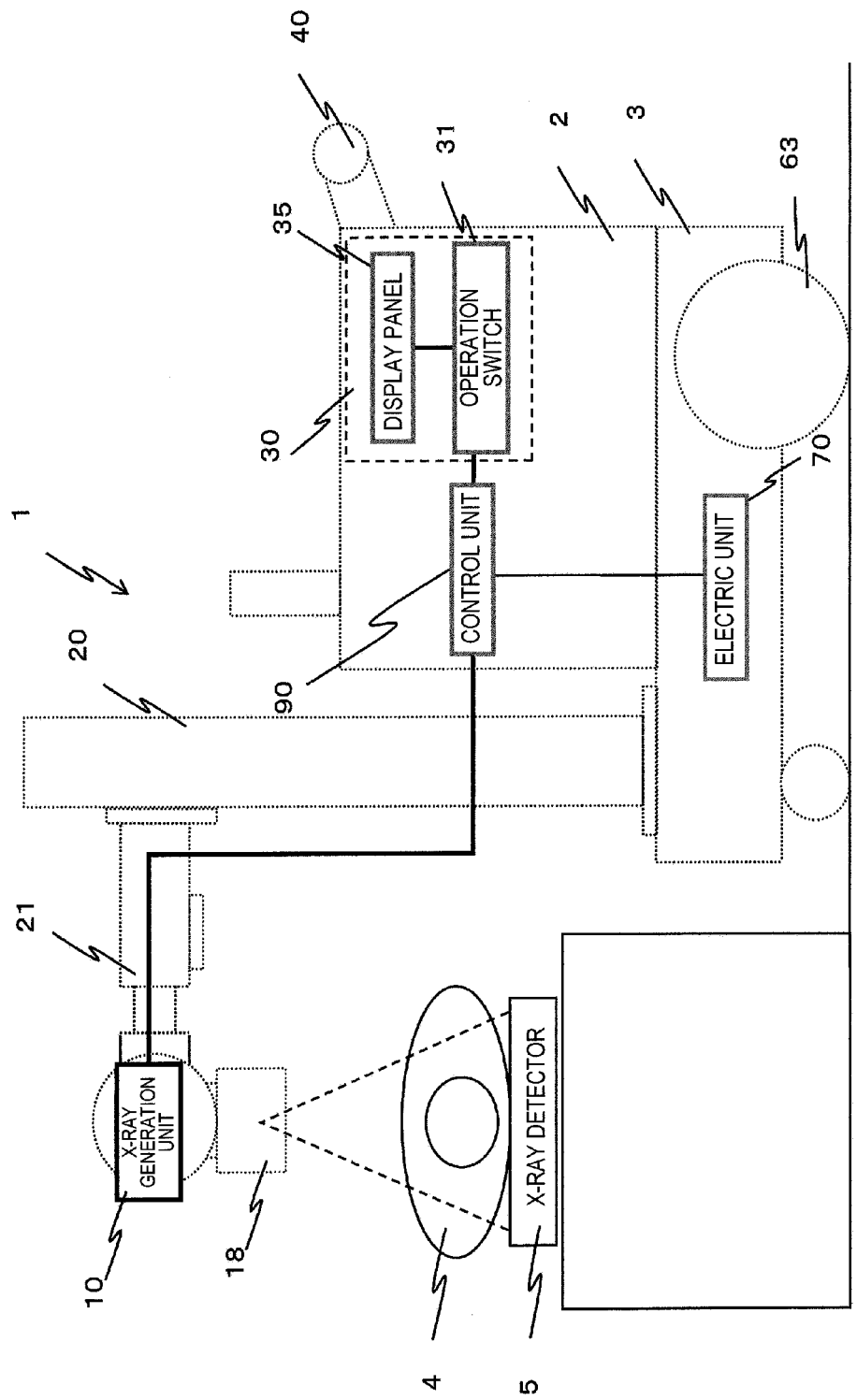
FIG. 2 is a schematic view of the contour and the blocks of the mobile X-ray device related to the present embodiment.

The configuration of the mobile X-ray device 1 related to the present embodiment will be described below based on FIG. 1 and FIG. 2. FIG. 1 is an external view of the mobile X-ray device related to the present embodiment, and FIG. 2 is a schematic view of the contour and the blocks of the mobile X-ray device related to the present embodiment.

The mobile X-ray device related to the present embodiment comprises mainly a main unit 2 and a mobile carriage 3 which is configured to travel and is equipped with the main unit 2. The mobile carriage 3 may be manually operated to travel, or may be operated to travel by a traveling motor 62 which drives wheels 63. In the front part of the mobile carriage 3, a column 20 is disposed upright. On the upper part of the column 20, an arm 21 formed by a Pantograph arm or a telescopic arm may be provided. An X-ray generator 10 configured to generate an X-ray and a beam limiting device 18 that limits the irradiation range of an X-ray are provided on the open-end side of the arm 21. By elongating, contracting or revolving the arm 21, the position of the X-ray generator 10 and the beam limiting device 18 are moved so that the X-ray is irradiated to an imaging region of an object 4. Also, the mobile X-ray device 1 can take the moving position and the imaging position by revolving the arm 21 while setting the longitudinal direction of the column 20 as the axis of revolution. FIG. 1 shows the moving position wherein the X-ray generator 10 is positioned at the upper part of the main unit 2, and FIG. 2 shows the imaging position wherein the X-ray generator 10 is positioned at the upper part of the object 4.

An X-ray detector 5 for detecting an X-ray which is transmitted through the object 4 is disposed at the position facing the X-ray generator 10 with the object 4 therebetween. Any device such as an FPD (Flat Panel Detector device), an imaging plate or an X-ray film may be used as the X-ray detector 5 as long as it can detect a transmitted X-ray and generate an X-ray image of an object. Also, an FPD may be electrically connected to the main unit 2 of the mobile X-ray device 1 by wire connection or wireless connection, or may be a so-called portable FPD which is configured separately from the mobile X-ray device 1. The mobile X-ray device 1 may also comprise an image processing device configured to generate an X-ray image based on the transmitted X-ray signals detected by the X-ray detector 5, an image reading device configured to read an X-ray image which is accumulated in an imaging plate as a latent image, and an image display device configured to display an X-ray image. In this manner, an X-ray image can be confirmed at the destination of the X-ray device. Also, in the case that the mobile X-ray device does not comprise an image processing device or an image reading device and an image display device, the size and the weight of the mobile X-ray device can be reduced in comparison to the one comprising these devices.

The main unit 2 comprises, at the opposite side of the column 20 (near the upper surface at the back part), an imaging panel (imaging condition setting unit) 30 for inputting the imaging condition for X-ray imaging and a traveling handle 40 for an operator to hold for driving the mobile X-ray device 1, and a control unit 90 for controlling the mobile X-ray device 1.

The imaging panel 30 comprises an operation switch 31 formed by keys for inputting imaging conditions and various switches and a display panel 35 configured to display the inputted imaging condition, perform alarm display indicating error classification to be described later or execution of recovery process, and perform error display indicating forcible termination of X-ray imaging. The beam limiting by the beam limiting unit 18 is driven in accordance with the X-ray irradiation range included in the imaging condition inputted from the operation switch 31.

A break for the mobile X-ray device 1 is provided to the traveling handle 40 though not shown in the diagram, and it is configured so that an operator can operate the break with the same hand which holds the traveling handle 40.

The control unit 90 is connected to the X-ray generator 10, the operation panel 30 and an electric unit 70 including a battery 71, and has the function, in the case that a temporal problem occurs in the X-ray generator during the X-ray irradiation process caused by the shortage of battery output or the use environment, to automatically interrupt the irradiation process on a temporary basis then restart the process. Further, the control unit 90 has a function, in the case that X-ray irradiation is interrupted due to battery power shortage, to automatically set the current value for generating an X-ray and resume the X-ray irradiation process, and to perform the X-ray irradiation process so as to ensure the radiation dosage in the initial imaging condition (the imaging condition set prior to the X-ray imaging) even when the current value is lowered. The configuration thereof will be described later.

Figure 3:
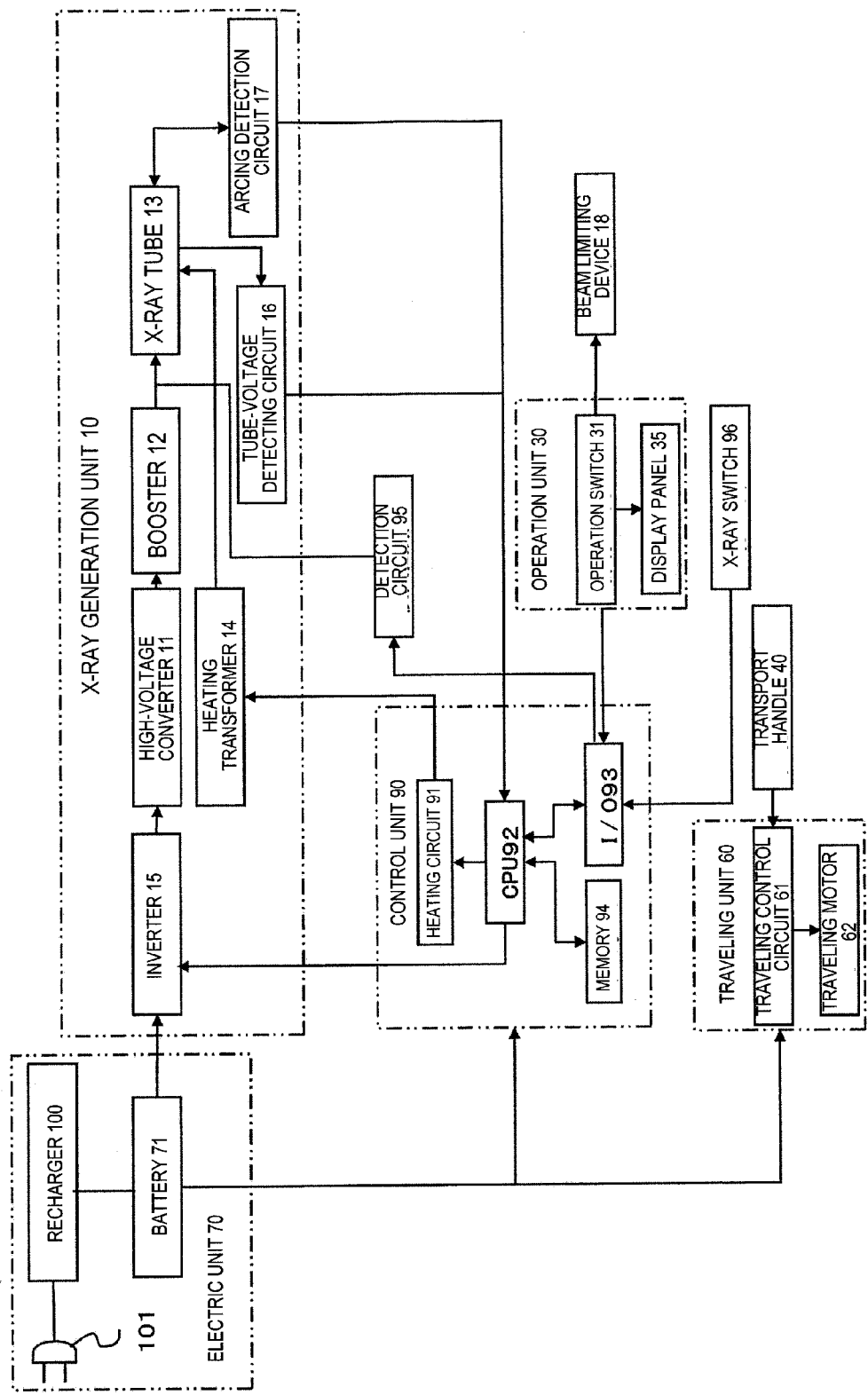
FIG. 3 is a functional block diagram of the mobile X-ray device related to the present embodiment.
Figure 4:
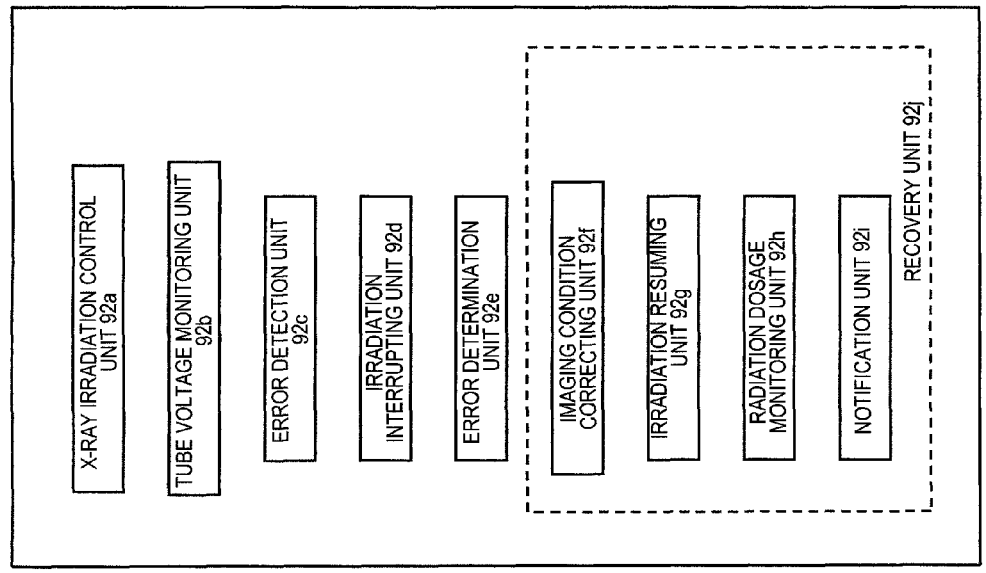
FIG. 4 is a block diagram of the control program for the mobile X-ray device related to the present embodiment.

Next, the internal constitution of the mobile X-ray device 1 will be described based on FIG. 3 and FIG. 4. FIG. 3 is a function block diagram of the mobile X-ray device related to the present embodiment. FIG. 4 is a block diagram for the control program for the mobile X-ray device related to the present embodiment.

The electric unit 70 of the mobile X-ray device 1 comprises the rechargeable battery 71, a recharger 100 for recharging the battery 71 and an AC plug 101. By connecting the AC plug 101 to an AC plug outlet at the destination of the X-ray device, the AC current acquired from the AC power source is converted into the DC current so as to recharge the battery 71. By providing the recharger 100 to the main unit 2, battery recharging can be executed at the destination of the mobile X-ray device. While the recharger 100 is disposed in the main unit 2 in the present embodiment, the battery 71 may be configured detachable from the mobile X-ray device 1, or the recharger 100 may be configured separately from the mobile X-ray device 1. Then the recharger 100 may be set at a predetermined position, for example the storage area of the mobile X-ray device 1 so that the battery 71 which is detached from the main unit 2 can be recharged there. In this manner, the size and the weight of the mobile X-ray device 1 can be reduced in comparison to the one equipped with the recharger 100.

The X-ray generator 10 is formed by an inverter-type X-ray generator, and the control unit 90 performs PWM control. Besides the PWM control method, the control unit 90 may perform the PAM control, or combination of the PWM control and the PAM control. The X-ray generator 10 comprises an inverter 15 configured to convert the DC current supplied from the battery 71 into the AD current, a high-voltage transformer 11 configured to transform the AC voltage of the inverter 15, a booster 12 to further raise the voltage of a high-voltage current from the high-voltage transformer 11, an X-ray tube 13 to which tube voltage is applied from the booster 12 and has a target (not shown) and a filament (not shown), a heating transformer 14 for transforming the current for heating the filament, a tube voltage detecting circuit 16 configured to detect the voltage applied to the X-ray tube 13, and an arcing detecting circuit 17 configured to detect a temporal discharge which is not enough to cause breakage of the X-ray tube 13 (hereinafter referred to as "arcing"). The X-ray tube 13 generates an X-ray by making the thermal electron emitted from the filament to strike the target.

The control unit 90 comprises a heating circuit 91 configured to control the heating transformer 14, a CPU (Central Processing Unit) 92, an I/O 93 connected to an X-ray switch 96 for an operator to execute input operation and an operation switch 31, and a memory 94 formed by a ROM in which the control program necessary for error detection and interruption/recovery process of X-ray imaging related to the present invention or a RAM to be used by the CPU 92 for executing the program or other processing.

Particularly, the mobile X-ray device in the present embodiment comprises the imaging condition setting unit 30 configured to set the imaging condition to be applied to X-ray imaging, the X-ray generator 10 configured to irradiate an X-ray according to the set imaging condition, the error detecting unit 92c configured to detect occurrence of an error by which the X-ray irradiation should be interrupted, the irradiation interrupting unit 92d configured to interrupt X-ray irradiation when the occurrence of an error is detected, and the recovery unit 92j configured to resume the X-ray irradiation for ensuring the X-ray amount defined by the imaging condition. The recovery unit 92j, for example irradiates an X-ray by setting the irradiation time of the X-ray to be resumed on the basis of the X-ray amount defined by the imaging condition or irradiates an X-ray by correcting the set imaging condition.

In concrete terms, as shown in FIG. 4, the mobile X-ray device in the present embodiment is formed by an X-ray irradiation control unit 92a configured to control the X-ray irradiation according to a predetermined imaging condition, a tube voltage monitoring unit 92b configured to detect and monitor the tube voltage of the X-ray tube 13 based on the detection signal from the tube voltage detecting circuit 16, the error detecting unit 92c configured to detect occurrence of an error by which the X-ray irradiation should be interrupted, the irradiation interrupting unit 92d configured to output an interruption signal to the X-ray irradiation control unit 92a upon the occurrence of an error, an error determination unit 92e configured to determine the kind of the occurred error, and the recovery unit 92j configured to execute the recovery process in accordance with the kind of error. The recovery unit 92j is formed by the imaging condition correcting unit 92f configured to correct the imaging condition prior to the interruption, an irradiation resuming unit 92g configured to output a cancellation signal for canceling the interruption to the X-ray irradiation control unit 92a, a radiation dosage monitoring unit 92h configured to monitor the X-ray irradiation dosage irradiated after resuming, and a notification unit 92i configured to notify that the recovery process is executed.

The CPU 92 reads out and executes the control program stored in the ROM for executing the error detection or the interruption/recovery process of the X-ray irradiation related to the present embodiment. While plural kinds of errors are detected by the error detecting unit 92c and the kind of error is determined by the error determining unit 92d in the present embodiment, it may also be configured that the content of the recovery process by the recovery unit 92j is associated with the signal indicating the occurrence of the error detected by the error detecting unit 92c so that the recovery process corresponding to the error can be executed. In this case, the error determination unit 92e may not be provided. Additionally, the error detecting unit 92 may be configured to detect one kind of error, and the error determination unit 92e is also not necessary in this case. Further, the error detecting unit 92c may comprise plural means for detecting one kind of error for the number of different kinds of errors so that the recovery process corresponding to the respective errors in the recovery unit 92j can be executed on the basis of the signal from the means for detecting one kind of error. The error determination unit 92e does not also have to be provided in this case.

The I/O93 is connected to a detecting circuit 95, and the detecting circuit 95 is connected to the X-ray tube 13. When an X-ray switch 96 is turned on, the irradiation signal of an X-ray is detected by the detecting circuit 95 via the I/O93, outputted to the X-ray tube 13, then the X-ray is irradiated from the X-ray tube 13.

The traveling unit 60 comprises a traveling control circuit 61 and a traveling motor 62 for driving the motor of wheels 63. Also, a transport handle 40 comprises a break (not shown in the diagram) for an operator to put break on the mobile X-ray device 1 while traveling. The traveling control circuit 61 controls this break and the traveling motor 62, controls to put break on the traveling motor 62 when the break is operated, and drives the traveling motor 62 when the break is cancelled, for running the mobile X-ray device 1.

Figure 5:
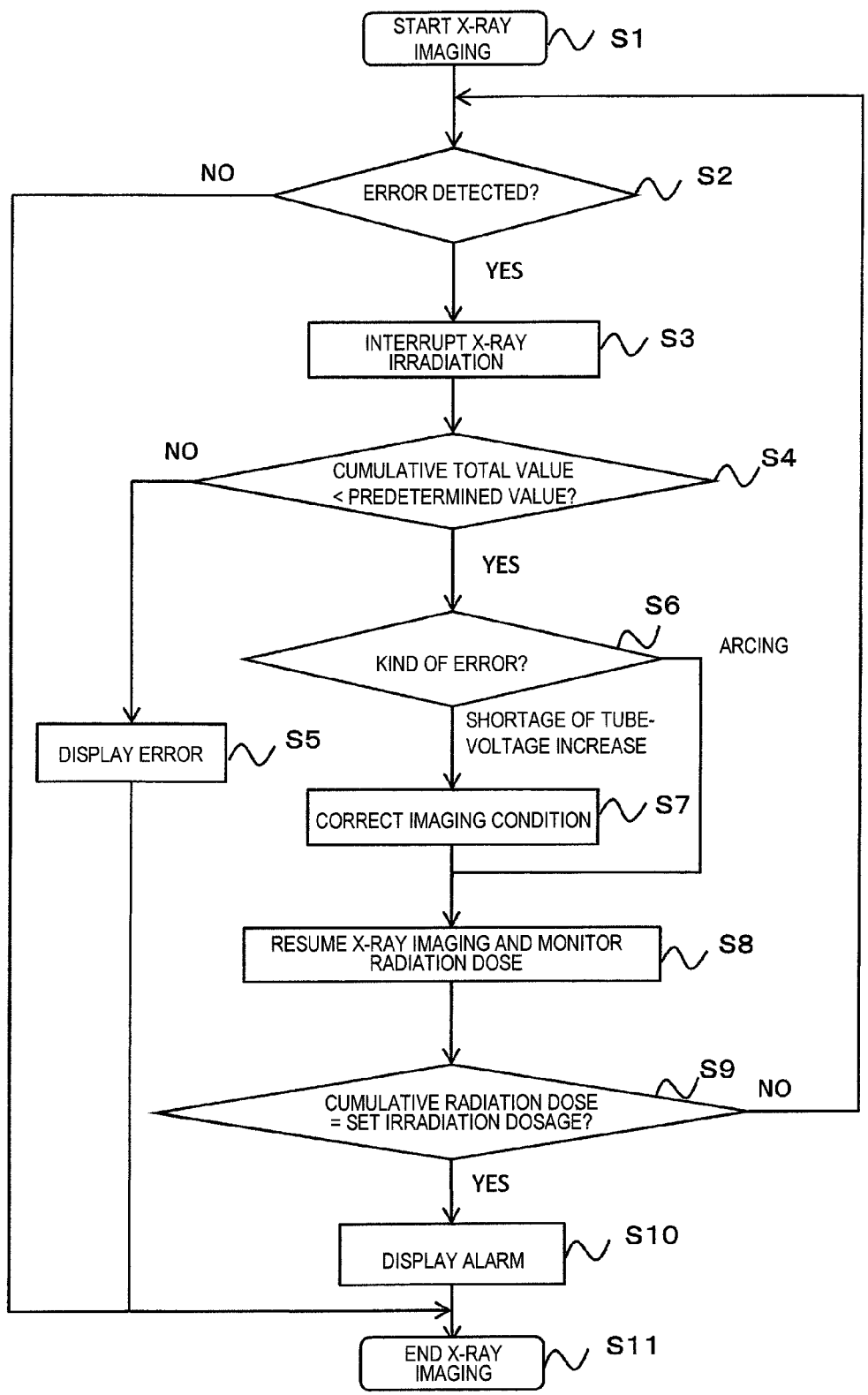
FIG. 5 is a flowchart showing the processing flow of the mobile X-ray device related to the present embodiment.

Next, the error detection and the recovery process related to the present embodiment will be described referring to FIG. 5. FIG. 5 is a flowchart showing the processing flow of the mobile X-ray device related to the present embodiment.

Prior to starting X-ray imaging, an operator operates the traveling handle 40 of the mobile X-ray device 1, makes the traveling motor 62 drive and transfers the mobile X-ray device 1 to the bedside where the object 4 is placed. The mobile X-ray device 1 is transferred in a moving position (refer to FIG. 1). After moving the device, the operator changes the position of the mobile X-ray device 1 to an imaging position (refer to FIG. 2) by revolving the arm 21. Then the operator moves the X-ray generator 10 to the imaging position which is at the upper part of the object 4. Also, the operator moves the X-ray detector 5 to the position facing the X-ray generator 10 with the object 5 therebetween. Then the operator inputs the imaging condition to be applied to the X-ray imaging using the imaging panel 30 provided to the main unit 2 of the mobile X-ray device 1. In the present embodiment, tube voltage (kV), tube current (mA) and irradiation time (s) are inputted as the X-ray imaging condition to be used. An X-ray dosage is defined by the product (mAs) of tube current (mA) and irradiation time (s), and calculated by the arithmetic device in the operation panel 30. While mAs is used as the physical quantity for defining the X-ray dosage in the present embodiment, other physical quantity may be used therefore. In the following description, the tube voltage (kV), tube current (mA), irradiation time (s), and radiation dosage (mAs) calculated by tube voltage (mA) and irradiation time (s) inputted prior to X-ray imaging are respectively referred to as the set tube voltage, set tube current, the set irradiation time and set radiation dosage. FIG. 5 will be described below along the respective steps.

(Step S1)

The operator pushes the X-ray switch 96 of the mobile X-ray device 1. The X-ray irradiation control unit 92a in the control unit 92 sets the output value of an X-ray from the X-ray generator 10 in accordance with the inputted imaging condition. At the time of the output of the X-ray, the X-ray irradiation control unit 92a controls the duty of the inverter 15 to make the tube voltage to be the set value. The X-ray from the X-ray generator 10 is irradiated to start the X-ray imaging (S1). The tube voltage monitoring unit 92b executes the comparison between the tube voltage detection value from the tube voltage detecting circuit 16 and the set tube voltage periodically or continually during the X-ray imaging.

(Step S2)

The X-ray imaging is normally completed (S11) when no error is detected by the error detecting unit 92c, and step S3 is carried out when an error is detected (S2). In the present embodiment, two kinds of errors are detected by the error detecting circuit 92c, which are the shortage of tube voltage and the arcing (temporal discharge).

While the X-ray irradiation control unit 92a controls the duty ratio with respect to the inverter 15, when the tube voltage monitoring unit 92b detects that the actual tube voltage can not be increased enough to the set tube voltage even when the duty ratio reaches the maximum, the tube voltage monitoring unit 92b outputs the signal showing the shortage of tube voltage to the error detecting unit 92c, and the error detecting unit 92c detects an error on the basis of the outputted signal. As for means to monitor tube voltage, besides software such as the tube voltage monitoring unit 92b, it may be configured using hardware by providing a tube voltage monitoring circuit (for example, a relay device) which is not shown in the diagram to the control unit 92. The tube voltage monitoring means also may be configured using both software and hardware. The error detecting unit 92c also detects occurrence of an error when an arcing detecting signal (a signal which indicates that a temporal discharge is detected) from the arcing detecting circuit 17 of the X-ray generator 10 is received.

(Step S3)

The error detecting unit 92c, when a signal indicating a shortage of tube voltage or an arcing detection signal is received, outputs an error occurrence signal to the irradiation interrupting unit 92d. The irradiation interrupting unit 92d transmits an interruption signal to the X-ray irradiation control unit 92a, and the X-ray irradiation control unit 92a interrupts the X-ray imaging (S3). Also, the error detecting unit 92c transmits the received signal indicating a shortage of the tube voltage or the arcing detection signal to the error determination unit 92e.

(Step S4)

The error detecting unit 92c counts the cumulative total value of the number of errors occurred during the X-ray imaging, and compares the cumulative total value and a predetermined value (for example, 3) which is the threshold value set for forcible termination (S4). Step S5 is carried out when the cumulative total value is a predetermined value or more, and step S6 is carried out when the cumulative total value of error occurrence is less than the predetermined value.

(Step S5)

The error detecting unit 92c outputs a forcible termination signal to the X-ray irradiation control unit 92a, and the X-ray irradiation control unit 92a executes error display on the display panel 35. Then the X-ray imaging is forcibly terminated.

(Step S6)

The error determination unit 92e determines the kind of the occurred error based on the signal received from the error detecting unit 92c in step S3 (S6). As the result of determination, the recovery process according to the kind of error is performed. That is, step S7 is carried out when the kind of error is a shortage of tube voltage, and step S8 is carried out when the kind of error is generation of arcing.

(Step S7)

The imaging condition correcting unit 92f calculates the value wherein the tube voltage from among the X-ray imaging condition applied prior to the interruption (equivalent to the imaging condition set and inputted by an operator in the recovery process for the first error, and equivalent to the imaging condition applied right before the interruption in the recovery process on and after the second error) is lowered for a preset predetermined ratio, for example 10-20%. The imaging condition correcting unit 92f, in the X-ray imaging in the recovery process, calculates the remaining irradiation time according to the lowering of the tube current value so as to fill the remaining amount wherein the radiation dosage irradiated right before the interruption is subtracted from the set radiation dosage corresponding to the imaging condition. The calculated current and the remaining irradiation time are outputted to the X-ray irradiation control unit 92a.

(Step S8)

After passing of a predetermined rest time from the interruption of X-ray imaging, the irradiation resuming unit 92g resumes the X-ray imaging (S8). The rest time here means the time necessary for recovering the circuit which paused due to interruption. Resuming of the X-ray imaging is executed by outputting a cancellation signal for canceling the interruption signal from the irradiation resuming unit 92g to the X-ray irradiation control unit 92a. The radiation dosage monitoring unit 92h monitors whether or not the radiation dosage of the X-ray irradiated in the recovery process reached the set radiation dosage by adding it to the radiation dosage from the start to the interruption of the X-ray imaging (S8).

In the case of the recovery process from the error due to a shortage of tube voltage increase (hereinafter referred to as "recovery process (1)"), the X-ray irradiation is resumed using the tube current calculated in step S7. Since the X-ray output of the X-ray irradiation in the recovery process (1) is small due to lowering of tube current, a long irradiation time is set to compensate. The irradiation resuming unit 92g outputs the signal for resuming X-ray imaging in accordance with the imaging condition corrected in step S7 with respect to the X-ray irradiation control unit 92a.

In the case of the recovery process from the error due to arcing (hereinafter referred to as "recovery process (2)"), the X-ray irradiation is resumed by the set tube current. The tube current of the X-ray irradiation in the recovery process (2) is the same as the tube current right before the interruption. In other words, when the X-ray imaging by the set tube current is interrupted due to detection of arcing, the imaging is resumed using the same tube current as the set tube current. Thus, the irradiation time of the recovery process (2) is the elapsed time from the start to the interruption of X-ray irradiation subtracted from the set irradiation time. The irradiation resuming unit 92g outputs the signal to resume the X-ray imaging in accordance with the imaging condition applied right before the interruption with respect to the X-ray irradiation control unit 92a.

(Step S9)

The radiation dosage monitoring unit 92h determines whether or not the radiation dosage of the X-ray irradiated in the recovery process reached the set radiation dosage by adding it to the radiation dosage from the start to the interruption of X-ray imaging. Step S10 is carried out if the result is positive, and step S2 is carried out to continue the X-ray imaging if the result is negative (S9).

(Step S10)

The notification unit 92i displays an alarm indicating that the recovery process is executed on the display panel 35 (S10). The alarm display may be performed by displaying an error code corresponding to the kind of error. Also, in place of the alarm display, a buzzer sound may be used to indicate that the recovery process is executed.

(Step S11)

The X-ray irradiation is completed (S11). After a user confirms an alarm display or a buzzer sound, if the mobile X-ray device 1 is the type that generated images can be confirmed right at the destination of the device (a visiting car equipped with a computed radiography device, or a visiting car equipped with FPD capable of reading and displaying digital images from FPD), he/she confirms at the destination if there is any problem with the images. If the mobile X-ray device is the type that the images cannot be confirmed at its destination, the user confirms the images after the visitation.

Figure 6:
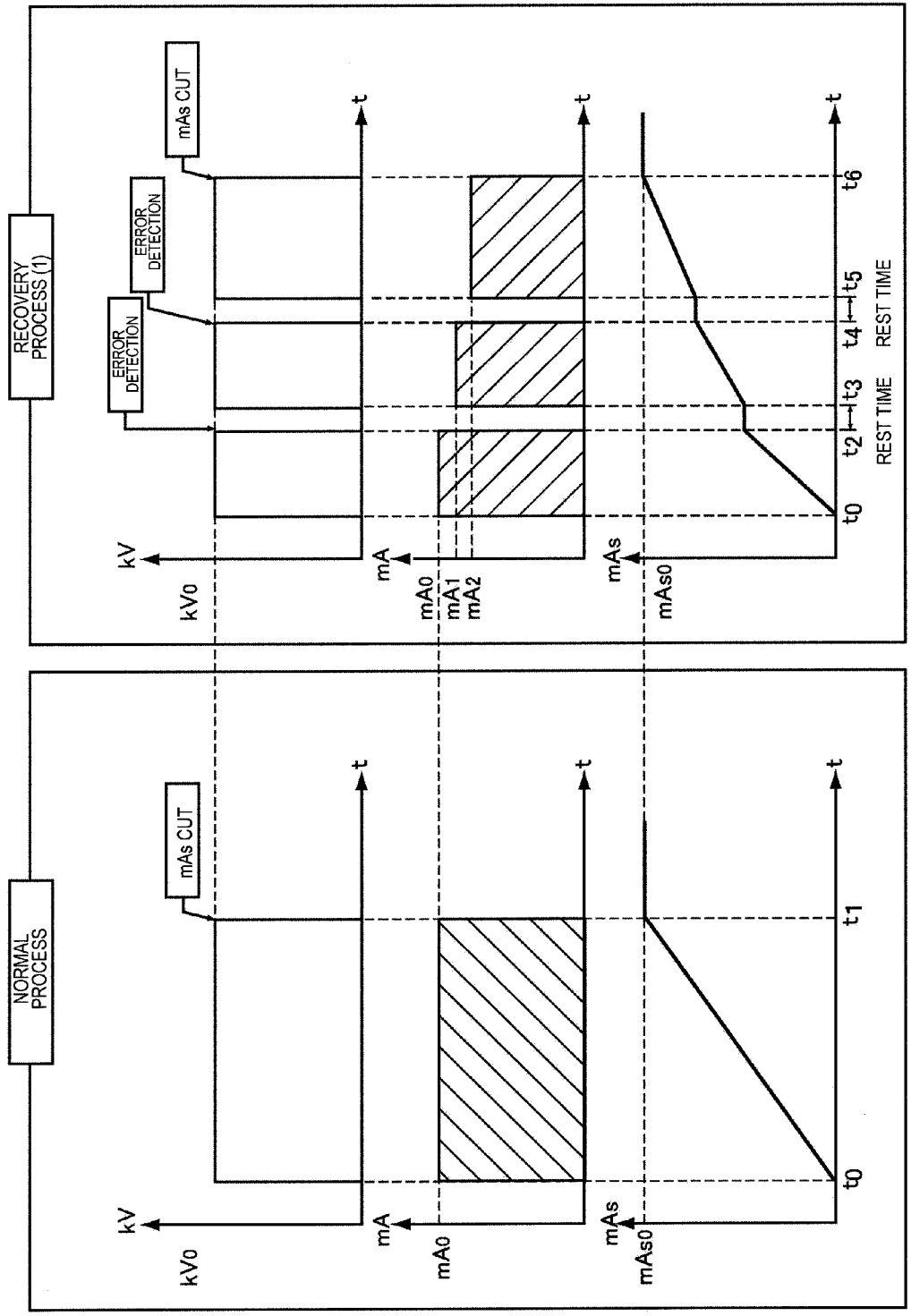
FIG. 6 is a graph showing the time change of tube voltage, the time change of tube current and the time change of radiation dosage during X-ray imaging in a normal process and a recovery process (1).

Next, the content of the recovery process from the error due to battery shortage will be described referring to FIG. 6. FIG. 6 is a graph showing the time change of tube voltage, time change of tube current and the time change of radiation dosage during X-ray imaging in the normal process and the recovery process (1). The radiation dosage is defined by the product mAs of tube current mA and time t, and the area of the shaded region in the graph of the middle part corresponding to tube current mA and time t is equivalent to tube current mAs. In FIG. 6, the normal process indicates in which case that no error is detected during X-ray imaging, and the recovery process (1) indicates the case in which two times of error are detected because the tube voltage could not reach the set value due to battery output shortage. In the normal process, from imaging start time t0 to imaging end time t1, X-ray radiation is executed using both the set values kV0 and mA0 for the tube voltage and the tube current from the start to the end of the X-ray imaging. In this case, radiation dosage mAs is the value multiplied by mA0 and irradiation time t1, and is equivalent to the area of the shaded part in which the lines are depicted from the upper right to the lower left in the graph showing the time change of tube current.

In the case of the recovery process (1), X-ray imaging is executed using the set values kV0 and mA0 from imaging start time t0 to time t2 at which the first error is detected. The X-ray imaging is once interrupted at time t2. Then after passing of a rest time, from time t3, the X-ray imaging is executed using the set value kV0 for the tube voltage and tube current value mA1 which is the value smaller than the set value mA0. When the second error is detected at time t4, the X-ray imaging is interrupted again. After passing of a rest time, from time t5, the X-ray imaging is executed using the set value kV0 for the tube voltage and tube current value mA2 which is the value smaller than mA1. Then when the total of the radiation dosage from the start of the X-ray imaging reaches the set radiation dosage value mAs0, the X-ray imaging is completed. The total of the irradiation time from the start to the end of X-ray imaging including the recovery process (1) ((t6−t0)−2*rest time) becomes longer than the set irradiation time (t1−t0), i.e. the irradiation time in the normal process. Since the total amount of radiation dosage in the normal process and the recovery process (1) is the same, the total of the area of the shaded region wherein the lines are depicted from the upper left to the lower right in the graph showing the time change of tube current in the recovery process (1) becomes the same as the area of the shaded part in the graph showing the time change of tube current in the normal process.

Figure 7:
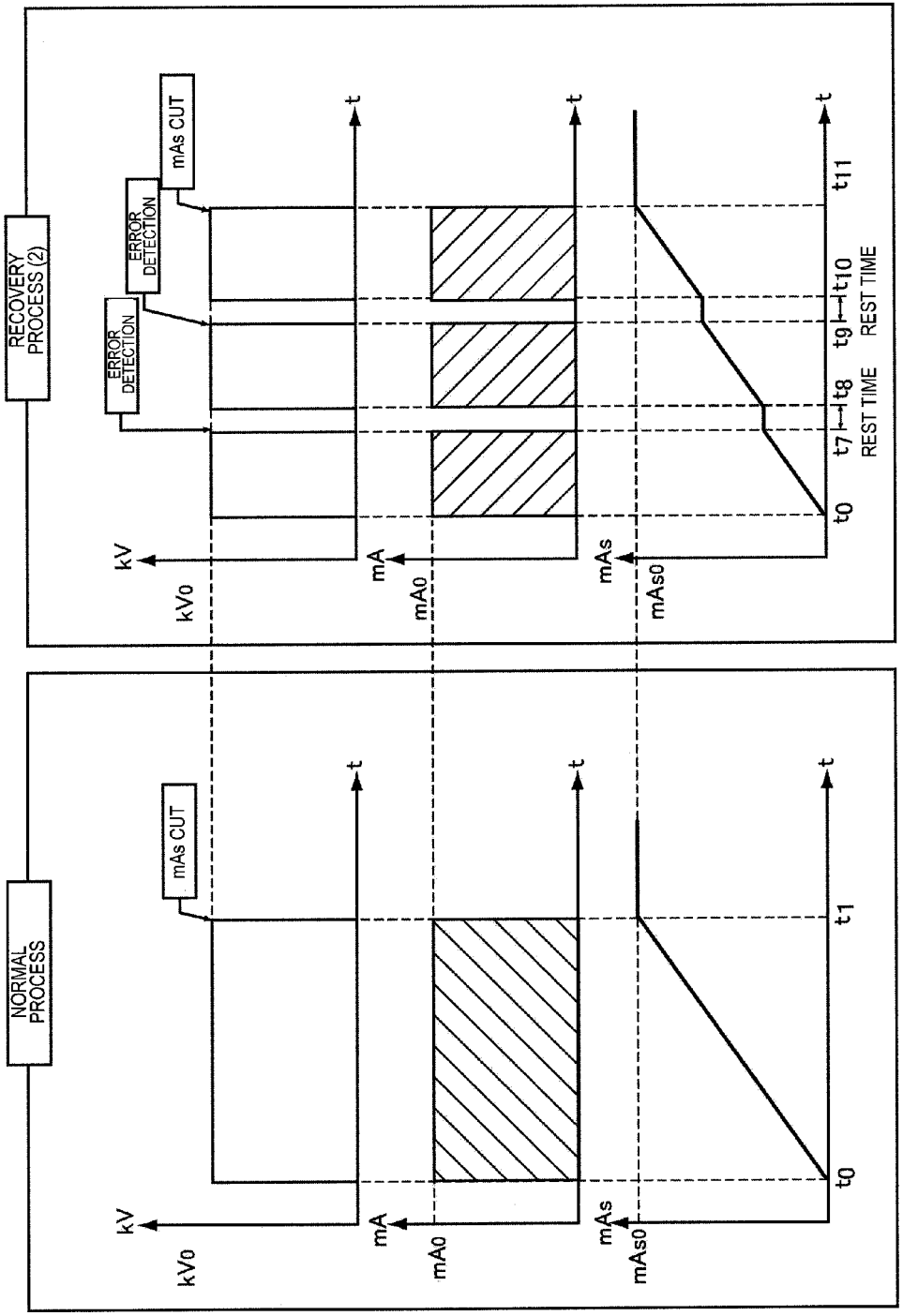
FIG. 7 is a graph showing the time change of tube voltage, the time change of tube current and the time change of radiation dosage during X-ray imaging in a normal process and a recovery process (2).

Next, the content of the recovery process from the error due to arcing will be described referring to FIG. 7. FIG. 7 is a graph showing the time change of tube voltage, the time change of tube current and the time change of radiation dosage during X-ray imaging in the normal process and the recovery process (2). In FIG. 7, the normal process indicates the case in which no error is detected during X-ray imaging, and the recovery process (2) indicates the case in which the error occurred due to arcing is detected two times.

In the case of the recovery process (2), X-ray imaging is executed using the set values kV0 and mA0 from the imaging start time t0 to the time t7 when the first error is detected. The X-ray imaging is once interrupted at time t7. Then after passing of a rest time, the X-ray imaging is resumed from time t8. After resuming, the X-ray imaging is also executed using the set tube voltage kV0 and the set tube current mA0. When the second error due to arcing is detected at time t9, the X-ray imaging is interrupted again. After passing of a rest time, from time t10, the X-ray imaging is resumed using the set value kV0 for the tube voltage and the set value mA0 for the tube current. Then when the total of the radiation dosage from the start of the X-ray imaging reaches the set radiation dosage mAs0, the X-ray imaging is completed. The total of the irradiation time from the start to the end of the X-ray imaging including the recovery process (2) ((t11−t0)−2*rest time) becomes the same as the set irradiation time (t1−t0). Since the total amount of the radiation dosage in the normal process and the recovery process (2) is the same, the total of the area of the shaded region wherein the lines are depicted from the upper left to the lower right in the graph showing the time change of tube current in the recovery process (2) becomes the same as the area of the shaded part in the graph showing the time change of tube current in the normal process.

While FIG. 6 and FIG. 7 show the case that the same kind of error occurred two times consecutively, the present invention can be applied even in the case that different kinds of errors occur consecutively. For example, the case may be that the first error is attributed to a shortage of tube current increase and the second error is attributed to arcing. In this case, X-ray irradiation is executed using the tube current lower than the set tube current at the time of the first recovery, and X-ray irradiation is executed using the tube current even lower than the previously mentioned set tube current which is the value right before the interruption at the time of the second recovery. If another error occurs following these errors, the irradiation is terminated forcibly since the cumulative total value surpasses the predetermined number of times.

In accordance with the mobile X-ray device related to the present embodiment, even in the case that the X-ray irradiation is interrupted, since the kind of error is determined and the X-ray imaging can be resumed by executing the recovery process according to the kind of error, it is also possible to execute the X-ray imaging using the result of the imaging prior to the interruption. Therefore, ineffective radiation exposure subjected to an object can be reduced, while saving an operator from the burden of restarting the X-ray imaging.

Though the present invention is applied to a mobile X-ray device in the present embodiment, it can also be applied to an X-ray apparatus of stationary type. In this case, even when an interruption occurs during X-ray imaging by an X-ray apparatus which is installed at the place where electric power supply is unstable or an interruption occurs due to arcing from an X-ray tube, the recovery process related to the present invention can be executed.

Also, while arcing and a shortage of tube voltage increase are exemplified as the kind of error in the above-described embodiment, the kind of error is not limited thereto.

DESCRIPTION OF REFERENCE NUMERALS

1: mobile X-ray device
2: main unit
3: traveling carriage
4: object
5: X-ray detector
10: X-ray generator
18: beam limiting device
20: column
21: arm
30: operation panel
40: transport handle
62: traveling motor
63: wheels
71: battery
90: control unit

The invention claimed is:
1. A mobile X-ray device comprising:
a main unit; and
a traveling unit configured to make the main unit travel,
wherein the main unit comprises:
an imaging condition setting unit configured to set an imaging condition to be applied to X-ray imaging;
an X-ray generator configured to irradiate an X-ray in accordance with the set imaging condition;

an error detecting unit, during the X-ray irradiation, configured to detect an occurrence of an error by which the X-ray irradiation should be interrupted;

an irradiation interrupting unit configured to interrupt the X-ray irradiation when the occurrence of an error is detected; and a recovery unit configured to resume the X-ray irradiation for ensuring the X-ray amount defined by the imaging condition, wherein the imaging condition includes a set value of the tube voltage to be applied to X-ray imaging, wherein the error detecting unit detects the case that the tube voltage applied to the X-ray generator does not reach the set value of the tube voltage as the occurrence of an error, and wherein the recovery unit resumes X-ray irradiation by applying the imaging condition in which the tube current is made lower than the tube current applied prior to the interruption.

2. The mobile X-ray device according to claim 1, further comprising:

a battery in which the electricity for applying voltage to the X-ray generator is stored.

3. The mobile X-ray device according to claim 1, further comprising:

a control unit configured to control the duty ratio of the an inverter; and a tube voltage monitoring unit configured to detect the tube voltage to be applied to an X-ray tube of the X-ray generator, wherein, in the condition that the duty ratio of the inverter is maximized by the control unit, when the tube voltage monitoring unit detects that the tube voltage applied to the X-ray tube does not reach the set value, the error detecting unit detects the occurrence of an error.

4. The mobile X-ray device according to claim 1, wherein the recovery unit resumes the X-ray irradiation by applying the X-ray irradiation time longer than the X-ray irradiation time which was not carried out due to the interruption, so as to compensate for the lowering of X-ray output caused by the lowered tube current of the case based on the tube current applied prior to the interruption.

5. A mobile X-ray device comprising:

a main unit; and a traveling unit configured to make the main unit travel, wherein the main unit comprises:

an imaging condition setting unit configured to set an imaging condition to be applied to X-ray imaging;

an X-ray generator configured to irradiate an X-ray in accordance with the set imaging condition;

an error detecting unit, during the X-ray irradiation, configured to detect an occurrence of an error by which the X-ray irradiation should be interrupted;

an irradiation interrupting unit configured to interrupt the X-ray irradiation when the occurrence of an error is detected;

a recovery unit configured to resume the X-ray irradiation for ensuring the X-ray amount defined by the imaging condition; and an error determination unit configured to determine the kind of error detected by the error detecting unit, wherein the recovery unit resumes the X-ray irradiation corresponding to the kind of error using the imaging condition which ensures the X-ray amount.

6. The mobile X-ray device according to claim 1, further comprising:

a notification unit configured to notify that X-ray irradiation is resumed by the recovery unit and/or the occurrence of an error.

7. A control method for X-ray irradiation comprising:

receiving input of imaging condition;

detecting, during X-ray irradiation, occurrence of an error by which the X-ray irradiation should be interrupted;

interrupting the X-ray irradiation when the occurrence of an error is detected; and resuming X-ray irradiation by correcting the imaging condition, wherein the imaging condition includes a set value of the tube voltage to be applied to X-ray imaging;

detecting when the tube voltage applied to the X-ray generator does not reach the set value of the tube voltage as the occurrence of an error; and resuming X-ray irradiation by applying the imaging condition in which the tube current is made lower than the tube current applied prior to the interruption.

* * * * *